US00PP26645P2

(12) United States Plant Patent
Lane et al.

(10) Patent No.: US PP26,645 P2
(45) Date of Patent: Apr. 26, 2016

(54) ***PRUNUS* TREE NAMED 'SPC103'**

(50) Latin Name: *Prunus avium*
Varietal Denomination: SPC103

(71) Applicant: Her Majesty The Queen In Right Of Canada as Represented by the Minister of Agriculture and Agri-Food, Ottawa (CA)

(72) Inventors: William David Lane, Summerland (CA); Richard MacDonald, Summerland (CA)

(73) Assignee: Her Majesty The Queen in Right of Canada as Represented by the Minister of Agricultural and Agri-Food, Ottawa (CA)

( * ) Notice: Subject to any disclaimer, the term of this patent is extended or adjusted under 35 U.S.C. 154(b) by 125 days.

(21) Appl. No.: 13/999,465

(22) Filed: Mar. 3, 2014

Related U.S. Application Data

(60) Provisional application No. 61/852,380, filed on May 15, 2013.

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

PUBLICATIONS

PLUTO Plant Variety Database Jul. 22, 2015 p. 1.*

* cited by examiner

*Primary Examiner* — Annette Para
(74) *Attorney, Agent, or Firm* — Penny J. Aguirre

(57) ABSTRACT

A new cultivar of *Prunus avium*, 'SPC103', characterized by its very late harvest season, its flowers that are self-fertile, its intermediate to high precocity of fruit bearing, its spreading growth habit with horizontal one year-old shoots, its fruit skin and flesh that is dark red-purple in color with juice that is high in sweetness, and its firm and moderately juicy fruit that is kidney to cordate in shape.

1 Drawing Sheet

Botanical classification: *Prunus avium.*
Variety denomination: 'SPC103'.

BACKGROUND OF THE INVENTION

The present invention relates to a new and distinct cultivar of *Prunus avium* and will be referred to hereafter by its cultivar name, 'SPC103'. 'SPC103' is a new cultivar of sweet cherry tree grown for fruit production.

The new cultivar of *Prunus* arose from a breeding program conducted by the Inventor at a research centre in Summerland, BC, Canada with the goal of developing a new cultivar of cherry tree that would extend the harvest season with fruit that was firm and well-sized with good stem pull retention and flowers that were self-fertile.

'SPC103' originated as a seedling that arose from seed planted from open pollination of 'Sweetheart' (not patented) in 1984. 'SPC103' (breeding ref. No. 13S-21-23) was selected as a single unique tree in 1991 from amongst the resulting seedlings.

Asexual propagation of the new cultivar was first accomplished by budding onto *Prunus avium* rootstock by the Inventor in Summerland, BC, Canada in 1997. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar as grown in test plots in Summerland, BC, Canada. These attributes in combination distinguish 'SPC103' as a unique cultivar of cherry tree.

1. 'SPC103' exhibits a very late harvest season; August 12$^{th}$ in Summerland, BC, Canada.
2. 'SPC103' exhibits flowers that are self-fertile.
3. 'SPC103' exhibits an intermediate to high precocity of fruit bearing.
4. 'SPC103' exhibits a spreading growth habit with horizontal one year-old shoots.
5. 'SPC103' exhibits fruit skin and flesh that is dark red-purple in color with juice that is high in sweetness.
6. 'SPC103' exhibits firm fruit that is moderately juicy and kidney to cordate in shape.

'Sweetheart', the female parent, is similar to 'SPC103' in being self-fertile but differs from 'SPC103' in having a tree habit that is more upright, longer fruit stalks, in having round shaped fruit, higher fruit set, and a fruit harvest maturity date about 9 days earlier. 'SPC103' can be most closely compared to the cultivars '13S2009' (U.S. Plant Pat. No. 20,551) and '13S2101' (U.S. Plant Patent pending)*. '13S2009' is similar to 'SPC103' in being self-fertile but differs from 'SPC103' in having longer fruit stalks, higher fruit set, and a fruit harvest maturity date that is about 2 days earlier. '13S2101' is similar to 'SPC103' in having a late harvest day, however '13S2101' differs most significantly in having fruit that is red in color and elongated cordate in shape.

* Examiner has permission to replace U.S. Plant Patent pending with an Application No. or Patent No. if applicable and delete this statement.

BRIEF DESCRIPTION OF THE DRAWING

The accompanying colored photograph illustrates the overall appearance and distinct characteristics of the fruit of 'SPC103' on a 15 year-old tree as grown in a trial plot in Summerland, B.C., Canada.

The photograph in FIG. 1 provides a view of a cluster of fruit of 'SPC103'. The colors in the photograph are as close as possible with the digital photography techniques available, the color values cited in the detailed botanical description accurately describe the colors of the cherry tree.

DETAILED BOTANICAL DESCRIPTION

The following is a detailed description of 15 year-old trees as grown in a trial plot in Summerland, B.C., Canada. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Plant type*.—Deciduous fruit bearing tree.

*Plant habit*.—Spreading with horizontal branching.

*Height and spread*.—Reaches about 3.0 m in height and about 5.4 m in width.

*Cold hardiness*.—U.S.D.A. Zone 4.

*Diseases and pests*.—No susceptibility or resistance to diseases or pests has been observed.

*Root description*.—Fibrous, freely branched.

*Propagation*.—Budding onto rootstock.

*Growth rate*.—Moderate to vigorous.

Trunk description:

*Size of trunk*.—27.7 cm in diameter measured 42 cm above soil level.

*Bark color*.—202C with horizontal streaks of 183B.

*Bark texture*.—Rough and peeled.

Description of dormant shoots (one year-old):

*Pubescence*.—Absent or very weak.

*Shoot size*.—Average of 40 cm in length and 65 mm cm in width.

*Anthocyanin presence*.—Little or none.

*Thickness of shoot at center of middle internode*.—Thin to moderate; Average of 4.64 mm.

*Bark color*.—152B.

*Shoot angle*.—Nearly horizontal.

*Lenticels*.—10 lenticels per 2 $cm^2$.

*Branch internode length*.—Long; average of 4.5 cm.

*Vegetative buds*.—Medium in size; 7.45 mm in length and 2.78 mm in width, conical in shape, held slightly out from shoot, support is medium.

Description of growing shoots:

*Color of growing tip of shoot*.—152B.

*Pubescence of shoots tip*.—Absent or very weak.

*Anthocyanin presence*.—Weak.

Foliage description:

*Leaf shape*.—Elliptic.

*Leaf division*.—Simple.

*Leaf base*.—Cuneate.

*Leaf apex*.—Acute and acuminate at very tip.

*Leaf fragrance*.—None.

*Leaf burst*.—Early in the beginning of full flowering.

*Leaf venation*.—Pinnate, not prominent, same as leaf color with the midrib on lower surface.

*Leaf margins*.—Dentate.

*Leaf arrangement*.—Alternate.

*Leaf aspect*.—Concave to flat and held horizontal to oblique downward in relation to shoot.

*Leaf attachment*.—Petiolate.

*Leaf surface*.—Glabrous on upper and lower surface with upper surface moderately to strongly glossy.

*Leaf size*.—Mature leaves average 16.7 cm in length and 7.6 cm in width.

*Leaf internodes*.—Average of 4.1 cm.

*Leaf color*.—Mature leaves upper surface; 139A, mature leaves lower surface; 147B, fall color occurs late in season.

*Petioles*.—Average of 3.9 cm in length and 2.21 mm in width, 144D in color with anthocyanin 166A, 2 nectaries are round and 200B in color, glabrous surface.

Inflorescence description:

*Blooming period*.—Mid in the bloom season in BC, Canada, just before '13S2009'.

*Inflorescence type*.—Clusters of single flowers.

*Inflorescence size*.—Average of 1.7 cm in length and 1.1 cm in width.

*Lastingness of inflorescence*.—Average of 7 to 10 days.

*Flower buds*.—Ovoid, sharp tip in shape, about 6.93 mm cm in length and 3.61 cm in width prior to opening, 175A in color.

*Flower type*.—Rotate corolla above an elongated calyx with stamens and pistil extended.

*Flower size*.—Average of 3.7 cm in diameter.

*Calyx*.—Comprised of sepals fused into an ovoid base with un-fused portions spreading at apex.

*Sepals*.—5, 184C in color, glabrous surface, about 6.04 mm in length with un-fused portions, entire glandular margin, attenuate apex, fused base.

*Petals*.—5, broadly elliptic in shape, un-fused, thin and papery substance, smooth margin, oblique base, emarginate apex, about 16.79 mm in length and 10.81 mm in width, 155C in color (upper and lower surface).

*Pedicels*.—Average of 38.41 mm in length, 10.81 mm in width, 144A in color, glabrous surface.

*Rachis*.—Glabrous surface, flowers lightly compacted with whorled arrangement.

Reproductive organs:

*Gynoecium*.—1 pistil about 1.33 cm in length and 1 mm in width extending beyond perianth, style is 176D in color, about 13.35 mm in length and 1 mm in length, stigma is about 1 mm in diameter and 201A in color, ovary is superior, glabrous and 141A in color.

*Androcoecium*.—Average of 29 stamens, base adnate to calyx, filaments are 159D in color, about 13.35 mm in length and 1 mm in width, anthers are 167A in color, dorsifixed, about 0.5 mm in length and in width, pollen is abundant in quantity and about 167A in color.

*Fertility*.—Self-fertile.

Fruit description:

*Fruit type*.—Drupe.

*Fruit shape*.—Kidney to cordate.

*Fruit apex*.—Flat and moderately low susceptibility to rain induced cracking.

*Fruit size*.—24.15 mm in length and 28.92 mm in width.

*Fruit firmness*.—Firm.

*Fruit set*.—Moderately high.

*Fruit stalk*.—Short and medium in thickness; 4.6 cm in length and 1.28 mm in wide, surface smooth, color 138A.

*Fruit bearing*.—Intermediate to high precocity.

*Skin color*.—187A when ripe with light colored dots.

*Harvest date*.—Very late harvest season; August 12$^{th}$ in Summerland, B.C., Canada.

*Skin surface*.—Glossy.

*Skin suture*.—Medium prominence.

*Flesh color*.—187B.

*Flesh texture*.—Fleshy, moderately juicy.

*Flavor*.—High degree of sweetness.

*Weight*.—10.7 g/drupe.

*Brix*.—20.34.

*Acidity*.—12.94 TA.

*Storage life*.—Up to 4-5 weeks at 0.5° C.

*Seeds*.—1 stone per drupe, 164C in color, medium to large in size; average of 11.09 mm in length and 10.12 mm in width and small to medium in comparison to fruit, shape; lateral view is symmetrical, semi adherent to flesh, front view is ovate, basal view is round, keel is moderately developed.

It is claimed:

1. A new and distinct cultivar of *Prunus* tree named 'SPC103' as herein illustrated and described.

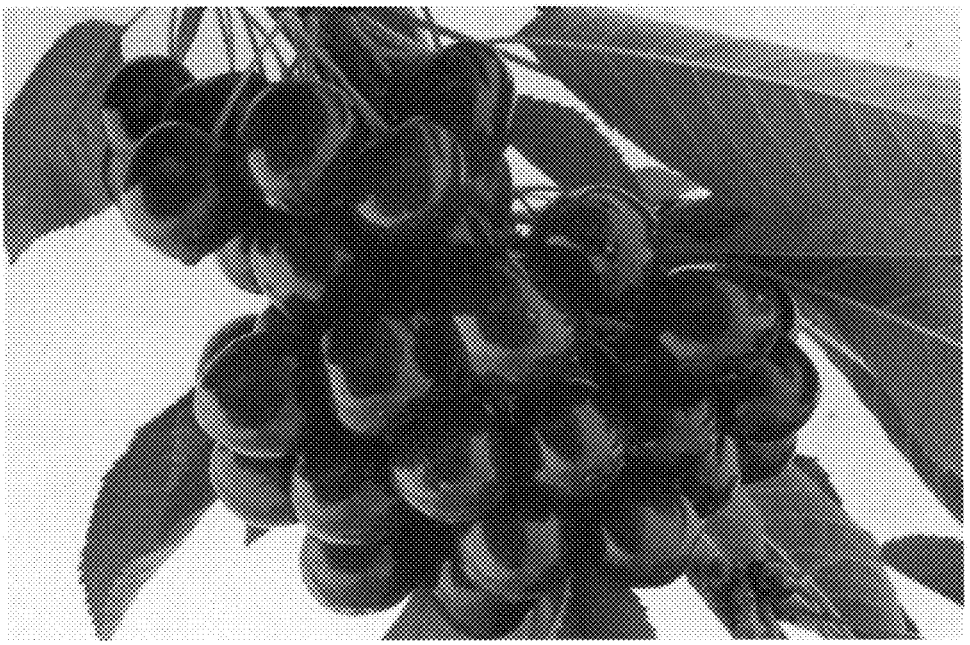

* * * * *